United States Patent
Berens et al.

(10) Patent No.: US 6,172,249 B1
(45) Date of Patent: Jan. 9, 2001

(54) CHIRAL LIGANDS FOR ASYMMETRIC CATALYSIS

(75) Inventors: Ulrich Berens; Mark Joseph Burk; Arne Gerlach, all of Cambridge (GB)

(73) Assignee: Chirotech Technology, Ltd. (GB)

( * ) Notice: Under 35 U.S.C. 154(b), the term of this patent shall be extended for 0 days.

(21) Appl. No.: 09/433,232

(22) Filed: Nov. 4, 1999

(30) Foreign Application Priority Data

Nov. 5, 1998 (WO) ................................. PCT/GB98/03321
May 12, 1999 (GB) ..................................................... 9911068

(51) Int. Cl.[7] ............................. C07F 9/50; C07F 17/02; C07C 69/66
(52) U.S. Cl. ........................... 556/14; 502/162; 544/106; 562/450; 560/179; 556/22
(58) Field of Search ................................ 556/13, 14, 22; 544/106; 502/162, 165, 166; 562/450; 560/179

(56) References Cited

U.S. PATENT DOCUMENTS

| | | | |
|---|---|---|---|
| 5,399,771 | 3/1995 | Cai et al. | |
| 5,563,309 | * 10/1996 | Togni et al. | 585/277 |
| 5,565,594 | * 10/1996 | Spindler et al. | 556/28 |
| 5,817,850 | * 10/1998 | Pastor et al. | 556/14 |
| 5,856,540 | * 1/1999 | Jendralla | 556/21 |
| 5,912,375 | * 6/1999 | Spindler et al. | 556/14 |
| 5,936,109 | * 8/1999 | Berens | 556/14 |

FOREIGN PATENT DOCUMENTS

| | | |
|---|---|---|
| 2262284 | 6/1993 | (GB) . |
| 9301199 | 1/1993 | (WO) . |
| 9802445 | 1/1998 | (WO) . |

OTHER PUBLICATIONS

Stephen R. Wilson, Alex Pasternak (1990) "Preparation of a New Class of C2–Symmetric Chiral Phosphines: The First Asymmetric Staudinger Reaction" 6139 Synlett (1990) Apr., No. 4, Stuttgart, DE.

* cited by examiner

Primary Examiner—Jean F Vollano
(74) Attorney, Agent, or Firm—Saliwanchik, Lloyd & Saliwanchik

(57) ABSTRACT

An enantiomerically enriched compound of formula (4)

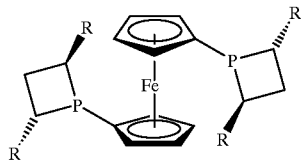

(4)

or the opposite enantiomer thereof, wherein R is $C_{1-10}$ alkyl. This compound, in the form of a transition metal complex, is useful as a catalyst for stereoselective hydrogenation.

9 Claims, No Drawings

CHIRAL LIGANDS FOR ASYMMETRIC CATALYSIS

FIELD OF THE INVENTION

This invention relates to phosphine ligands and metal complexes thereof, and to the use of the complexes as catalysts for asymmetric hydrogenation processes.

BACKGROUND TO THE INVENTION

The list of available chiral ligands for asymmetric catalytic transformations continues to grow at a rapid pace, and yet many desirable reactions remain impractical due to the limitations of currently available catalyst systems. In particular, achieving both high rates and high enantio selectivities in catalysis remains a serious challenge that continues to present the principal obstacle to the development of cost-effective asymmetric catalytic processes.

Burk, in Handbook of Chiral Chemicals, ed. Ager, Marcel Dekker, Inc., New York (1999), Chapter 18: 339–59, and references cited therein, reports that ligands composed of 2,5-disubstituted phospholane groups may bestow significant advantages in terms of enantioselectivities in asymmetric catalytic hydrogenation reactions. Unfortunately, catalysts that rendered the highest selectivities (e.g. DuPHOS-Rh and BPE-Rh) often displayed low catalytic rates in the hydrogenation of certain functional groups (e.g. ketones, hindered alkenes, etc.). Burk and Gross, Tet. Lett. 35:9363 (1994), report that reaction rates could be accelerated by the introduction of more flexible ligand backbones (e.g. 1,3-propano and 1,1'-ferrocenyl bridges), but enantioslectivities fell.

WO-A-98/02445 describes chiral phosphetane ligands as defined by general formula 1, or the opposite enantiomer thereof, wherein R groups are each independently H, alkyl, cycloalkyl, aryl or alkaryl, provided that $R^1$ and $R^2$ are both not H, and X is any group capable of forming a stable bond to phosphorus. In particular, WO-A-98/02445 highlights the synthetic utility of rhodium complexes of monophosphetanes of formula 2, wherein $R^1=R^2$, in comparison with five-membered ring analogues of formula 3

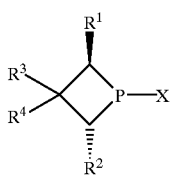

(1)

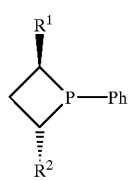

(2)

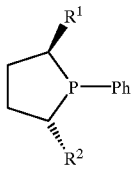

(3)

WO-A-99/02444 (published after the priority dates claimed in this Application) describes an improved process for the preparation of cyclic phosphines. This involves the addition of strong base to a preformed mixture or reaction product of a primary phosphine and an alkylating agent.

SUMMARY OF THE INVENTION

Novel ligands according to the present invention are bis(dialkyiphosphetano)ferrocenes of formula 4

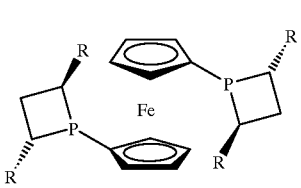

(4)

wherein R is linear or branched alkyl (including the opposite enantiomers thereof). Unexpectedly, it has been found that these bis(dialkylphosphetano)ferrocenes have especial utility as components of catalysts for asymmetric synthesis. In particular, their transition metal complexes give superior performance in the asymmetric hydrogenation of certain prochiral substrates, in terms of improved enantioselectivity and catalytic activity, when compared with equivalent complexes of alternative known chiral pbosphine ligands.

DESCRIPTION OF THE INVENTION

Preferred ligands of the present invention arc those where R is linear alkyl, e.g. linear $C_{1-4}$ alkyl, more preferably methyl or ethyl and rhodium(I) complexes thereof. It will be understood by those skilled in the art that the term "alkyl" does not necessarily comprise C and H only, provided that any substituents have no effect on the function of the ligands.

This invention involves asymmetric hydrogenation which is applicable to a variety of substrates, especially those that might otherwise require forcing conditions, or where other ligands give no or little conversion. Examples of such substrates are those with C=C bonds, e.g. tetrasubstituted alkenes and also itaconic acid derivatives such as esters (whether or not β-substituted or β,β'-disubstituted), those with C=O bonds, e.g. ketones and α-ketoacids, and those with C=N bonds, e.g. oximes and imines that can be converted to chiral hydroxylamines and chiral amines, respectively. As is evident from the Examples below, a particular class of substrates that can be hydrogenated according to this invention, has the partial formula C=C(C=O)—C—C=O, especially C=C(COOH)—C—C=O.

The hydrogenation reaction may be conducted under conditions that are known to, or can be determined by, those skilled in the art. Examples are given below.

The novel 1,1'-bis(phosphetano)ferrocenes may be prepared by known procedures, or as generally disclosed in WO-A-99/02444. Suitable reactants are of the formulae

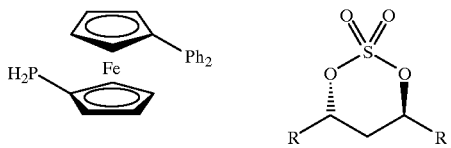

which may be reacted in the presence of an alkyllithium, in THF. The cyclic sulfates may be prepared starting from enantiomerically pure 1,3-diols. These diols may be prepared through asymmetric hydrogenation of 1,3-diketones using well-documented procedures involving catalysts such as Ru-BINAP catalysts; see Noyori et al, JACS 110:629 (1988). Subsequently, the diols may be converted to 1,3-diol cyclic sulfates through treatment with thionyl chloride followed by Ru-catalyzed oxidation with sodium periodate. Reaction between the cyclic sulfates cyclic sulfates and 1,1'-bis(phosphino)ferrocene in the presence of a strong base such as s-BuLi gives the desired ligands (4). For utilisazion as catalysts in asymmetric hydrogenation, rhodium complexes of (4) are of the form $[Rh(4)(COD)]BF_4$, which are prepared by sequential reaction of Rh(COD)acac with COD (1,5-cyclooctadiene), $HBF_4$—$OEt_2$ and the ligand (4).

The invention is further illustrated by the following Examples. Examples 1–5 describe the preparation of ligands of formula (4). Examples 6–10 describe the preparation of the corresponding rhodium complexes. Examples 11–15 describe the use of the complexes as catalysts for asymmetric hydrogenation process and include comparisons with rhodium complexes of other chiral ligands. Hydrogenation conditions for these examples are shown in individual equations (80 psi=550 kPa). In all cases, rhodium complexes are of the form $[Rh(Ligand)(COD)]BF_4$ wherein Ligand is a chiral diphosphine ligand. Ligands are denoted by acronyms, as follows:

Fc-4-Me, Fc-4-Et, Fc-4-Pr, Fc-4-i-Pr and Fc-4-t-Bu are ligands (4) of the present invention; and Fc-5-Me and Fc-5-Et are analogues of (4) containing five-membered phospholane rings, as described by Burk and Gross, supra.

For definitions of BINAP, bppm DIP AMP and DPHOS, see Noyori, in Catalytic Asymmetric Synthesis, ed. Ojima, VCH Inc., New York (1993).

For a definition of PHANEPHOS, see Pye ei al., JACS 119:6207 (1997).

General Procedure 1 Ligands

A 500 ml three-necked flask was equipped with magnetic stirrer bar, a dropping funnel on the middle neck, a reflux condenser with bubbler and a septum on the third neck. In this flask was made up under nitrogen a solution of 8.4 mmol of the cyclic sulphate in 250 mL of THF. The flask was immersed in an ice bath, and the solvent was degassed by bubbling nitrogen through it using a capillary bleed. In the dropping funnel was prepared a solution of 35.2 mmol of s-BuLi in 50 mL of pentane under nitrogen. After 45 minutes of solvent degassing, 2.0 g (8 mmol) of 1,1'-bis(phosphino) ferrocene was added via a syringe to the THF-solution. Then vigorous stirring was started, and the diluted solution of the s-BuLi was added dropwise into the vortex. At the end of the addition, the reaction was quenched by the addition of ca 3 mL of methanol, and the solvent was removed in vacuum. To the residue was added water (ca. 150 mL), and then the ligand was extracted into pentane (2×100 mL). Evaporation of the solvent from the dried combined organic layers provided the crude product which was purified further by recrystalisation from methanol.

EXAMPLE 1

1,1'-Bis((2R,4R)-2,4-dimethyl-phosphetano)ferrocene (referred to herein as (R,R)-Fc-4-Me) was prepared by General Procedure 1, in a crude yield of 3.00 g. Recrystallisation from ca 15 mL of methanol gave 0.85 g (27.5%) of yellow plates. $^{31}$P-NMR (CDCl$_3$, 162 MHz) δ 16.01.

EXAMPLE 2

1,1'-Bis((2R,4R)-2,4-diethyl-phosphetano)ferrocene (referred to herein as (R,R)-Fc-4-Et) was prepared by General Procedure 1, in a crude yield of 3.2 g. Recrystallisation from 30 mL of methanol gave 1.06 g (30%) as very fine yellow needles. $^{31}$P-NMR (CDCl$_3$, 162 MHz) δ 13.10.

EXAMPLE 3

1,1'-Bis((2R,4R)-2,4di-n-propyl-phosphetano)ferrocene (referred to herein as (R,R)-Fc-4-Pr) was prepared by General Procedure 1, in a crude yield of 3.2 g Recrystallisation from a mixture of methanol and ethanol gave 1.34 g (33%) as a yellow solid. $^{31}$P-NMR (CDCl$_3$, 162 MHz) δ 16.04.

EXAMPLE 4

1,1'-Bis((2R,4R)-2,4-diisopropyl-phosphetano)ferrocene (referred to herein as (R,R)-Fc-4-i-Pr) was prepared by General Procedure 1, in a crude yield of 4.0 g Recrystallisation from 20 mL of methanol gave 2.85 g (71..5%) as very fine yellow needles. $^{31}$P-NMR (CDCl$_3$, 162 MHz) δ 9.74.

EXAMPLE 5

1,1'-Bis((2R,4R)-2,4-di-tert-butyl-phosphetano)ferrocene (referred to herein as (R,R)-Fc-4-Bu) was prepared by General Procedure 1, in a crude yield of 3.4 g Recrystallisation from 50 mL of methanol gave 1.12 g (25%) as very fine yellow needles. $^{31}$P-NMR (CDCl$_3$, 162 MHz) δ 7.63.

General Procedure 2 Rh(I)-tetrafluoroborate catalysts

In a Schlenk flask was made up, under nitrogen, a ca. 0.5 N solution of one equivalent of [Rh(COD)acac] in THF. To this solution was added two equivalents of 1,5-cyclooctadiene, and when the mixture had warmed to 50° C., one equivalent of $HBF_4$-$OEt_2$ was added dropwise as a ca. 1 N solution in THF. A slurry of $[Rh(COD)_2]BF_4$ was formed, and to this was added dropwise a solution of one equivalent of the ligand. The $[Rh(COD)_2]BF_4$ dissolved gradually, and the colour of the solution changed from brown to bright red-orange. When the addition was complete, the mixture was kept stirring for another ten minutes. Then ether was added dropwise to the stirred solution until the mixture become turbid. When the catalyst had started to crystallise, more ether was added into the reaction mixture to complete the precipitation of the catalyst. The product was filtered off under nitrogen, washed with a mixture of THF/ether 6:4 v:v until the filtrate was colourless, and the filtered solid was then dried in vacuo to constant weight.

EXAMPLE 6

[(2R,4R)-Fc-4-Me]-(1,5-cyclooctadiene)-rhodium(I) tetrafluoroborate was obtained by General Procedure 2, from 0.5 g of ligand in a yield of 0.57 g (64.3%). $^{31}$P-NMR (CDCl$_3$, 162 MHz) δ61.46 (d, $J_{P,Rh}$=146.5 Hz).

EXAMPLE 7

[(2R,4R)-Fc-4-Et]-(1,5-cyclooctadiene)-rhodium(I) tetrafluoroborate was obtained by General Procedure 2, from 0.6 g of ligand in a yied of 0.90 g (89%). $^{31}$NMR (CDCl$_3$ 162 MHz): δ 72.15 (d, $J_{P,Rh}$=146 Hz).

EXAMPLE 8

[(2R,4R)-Fc-4-Pr]-(1,5-cyclooctadiene)-rhodium(I) tetrafluoroborate was obtained by General Procedure 2, from 1.1 g of ligand in a yield of 0.40 g (21%). $^{31}$P-NMR (CDCl$_3$ 162 MHz): δ 53.27 (d, $J_{P,Rh}$=146 Hz).

EXAMPLE 9

[(2R,4R)-Fc-4-i-Pr]-(1,5-cyclooctadiene)-rhodium(I) tetrafluoroborate was obtained by General Procedure 2, from 1.0 g of ligand in a yield of 1.35 g (84%). $^{31}$P-NMR (CDCl$_3$ 162 MHz): δ 43.86 (d, $J_{P,Rh}$=145.6 Hz).

EXAMPLE 10

[(2R,4R)-Fc-4-t-Bu]-(1,5-cyclooctadiene)-rhodium(I) tetrafluoroborate was obtained by General Procedure 2, from 1.12 g of ligand in a yield of 0.92 g (53%). $^{31}$P-NMR (CDCl$_3$ 162 MHz): δ 38.27 (d, J=141 Hz).

EXAMPLE 11

Hydrogenation of α-acetamidocinnamic Acid

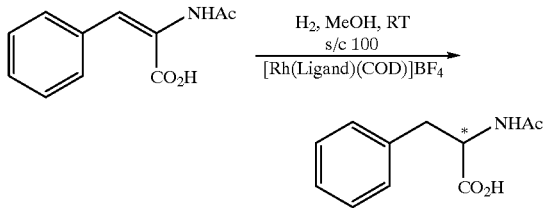

TABLE 1

| entry | Ligand | % ee |
|---|---|---|
| 1 | (R,R)-Fc-4-Me | 75 |
| 2 | (R,R)-Fc-5-Me | 69 |
| 3 | (R,R)-Fc-4-Et | 90 |
| 4 | (R,R)-Fc-5-Et | 58 |

As shown in table 1, rhodium complexes containing the ligands (R,R)-Fc-4-Me and (R,R)-Fc-4-Et (entries 1 and 3) gave superior enantioselectivities for this process, compared to those containing (R,R)-Fc-5-Me and (R,R)-Fc-5-Et (entries 2 and 4).

EXAMPLE 12

Hydrogenation of Dimethyl Itaconate

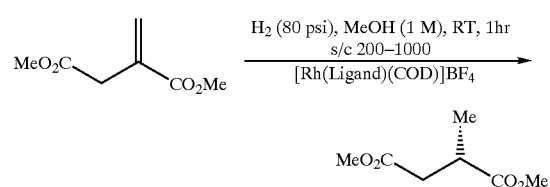

TABLE 2

| entry | Ligand | % ee |
|---|---|---|
| 1 | (R,R)-Fc-4-Me | 91 |
| 2 | (R,R)-Fc-4-Et | 96 |
| 3 | (R,R)-Fc-4-Pr | 94 |
| 4 | (S,S)-Fc-4-i-Pr | 78 |
| 5 | (S,S)-Fc-5-Me | 70 |
| 6 | (S,S)-Fc-5-Et | 66 |
| 7 | Et-DuPHOS | 97 |
| 8 | DIPAMP | 85 |
| 9 | PHANEPHOS | 12 |
| 10 | bppm | 69 |

Table 2 shows that ligands of the invention, especially Fc-4-Et and Fc-4-Pr (entries 2–3), are very effective for this transformation, affording the product with enantioselectivity comparable to that achieved with Et-DuPHOS (entry 7). All other ligands gave inferior performance. A striking difference is observed between results achieved with the novel ligands, especially n-alkyl variants, and the structural analogues Fc-5-Me and Fc-5-Et (entries 5–6). The advantages conferred by the phosphetane ligands are evident, although the reason for such a significant increase in selectivity upon moving from a five-membered ring to a four-membered phosphorus heterocycle is unclear.

EXAMPLE 13

Hydrogenation of in Inverse Itaconate Ester

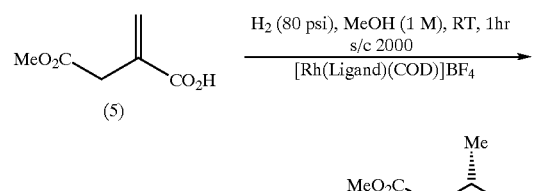

TABLE 3

| entry | Ligand | % Conversion | % ee |
|---|---|---|---|
| 1 | (R,R)-Me-DuPHOS | 2 | 41 |
| 2 | (S,S)-Et-DuPHOS | 3 | 74 |
| 3 | DIPAMP | 3 | 32 |
| 4 | bppm | 80 | 25 |
| 5 | PHANEPHOS | >99 | 26 |
| 6 | (R,R)-Fc-4-Me | >99 | 89 |
| 7 | (R,R)-Fc-4-Et | >99 | 94 |
| 8 | (R,R)-Fc-4-Pr | >99 | 95 |

TABLE 3-continued

| entry | Ligand | % Conversion | % ee |
|---|---|---|---|
| 9 | (R,R)-Fc-5-Me | >99 | 43 |
| 10 | (R,R)-Fc-5-Et | >99 | 33 |

Table 3 reports the result obtained from asymmetric hydrogenation of "inverse" itaconate (5). The term "inverse" refers to the protection pattern of the itaconate, and implies an inverse of ester/acid protection relative to standard Stobbe-derived itaconates. It can be seen that the rhodium complexes of DuPHOS, DIPAMP and bppm ligands were inadequate with regard to both catalytic efficiency and enantioselectivity (entries 1–4). In order to test this further, the rhodium catalyst of the PHANEPHOS ligand did render acceptable rates, although ee's were low (entry 5). Likewise, catalysts bearing the Fc-5-Me amd Fc-5-Et ligands were highly active, yet performed poorly in terms of enantioselectivity (entries 9–10). Catalysts based on the novel ligands, especially Fc-4-Et and Fc-4-Pr, were very efficient in this process (entries 6–8).

EXAMPLE 14

Hydrogenation of a β-substituted Inverse Itaconate Ester

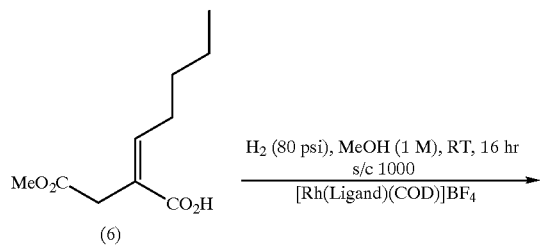

TABLE 4

| entry | Ligand | % Conversion | % ee |
|---|---|---|---|
| 1 | Fc-4-Et | 60 | 91 |
| 2 | Fc-4-Pr | 75 | 93.5 |
| 3 | bppm | 21 | 3 |

Table 4 shows results from hydrogenation of the β-substituted inverse itaconate ester (6). Rhodium complexes of Fc-4-Et and Fc-4-Pr ligands were found to promote highly enantioselective hydrogenation with good substrate conversion (entries 1–2). In contrast the bppm catalyst was completely ineffective (entry 3).

EXAMPLE 15

Hydrogenation of β-substituted Inverse Itaconate Amides

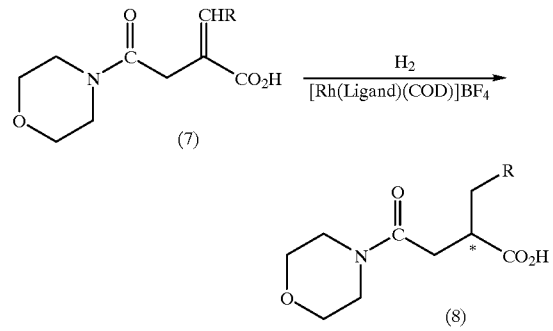

This process was investigated, since amidosuccinate derivatives of type (8) have served as versatile peptidomimetic intermediates for the construction of various important drug candidates. The substrates represented by formula (7) are another class of "inversely"-protected itaconates.

Results are shown in Tables 5–7. For the specific substrates (9) and (10), tables 5 and 6 compare the performance of the rhodiun complex of Fc-4-Et with rhodium complexes of a broad range of alternative ligands. The novel Fc-4-Et catalyst was markedly superior in terms of both rates and enantioselectivities. As shown by the result in Table 7, this catalyst can also accommodate a broad range of β-substiuents in the substrate; in each case, rapid substrate conversion and high enantioselectivity was observed.

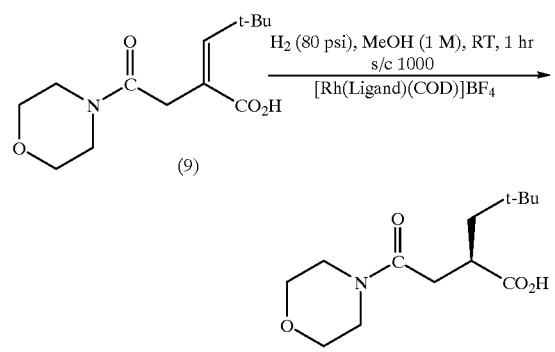

TABLE 5

| entry | Ligand | % Conversion | % ee |
|---|---|---|---|
| 1 | Fc-4-Et | >99 | 99 |
| 2 | Fc-5-Et | 45 | 41 |
| 3 | Et-DuPHOS | 7 | 89 |
| 4 | DIPAMP | 50.5 | 89 |
| 5 | PHANEPHOS | 50 | 69 |
| 6 | bppm | 98 | 78 |

TABLE 5-continued

| entry | Ligand | % Conversion | % ee |
|---|---|---|---|

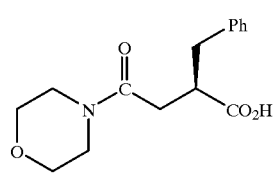

(10)

TABLE 6

| entry | Ligand | % Conversion | % ee |
|---|---|---|---|
| 1 | Fc-4-Et | >99 | 98 |
| 2 | Fc-5-Et | 55 | 70 |
| 3 | Et-DuPHOS | 5 | 85 |
| 4 | DIPAMP | 10 | 87 |
| 5 | PHANEPHOS | 60 | 62 |

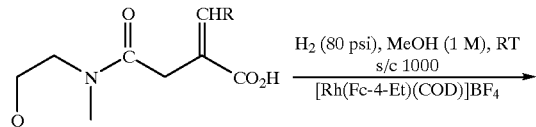

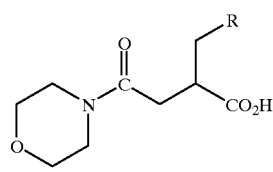

TABLE 7

| entry | R | τ (min) | % ee |
|---|---|---|---|
| 1 | Ph | 60 | 98 |
| 2 | t-Bu | 60 | 99 |
| 3 | i-Pr | 30 | 94 |
| 4 | o-Br—Ph | 30 | 95 |
| 5 | o-MeS—Ph | 15 | 97 |
| 6 | o-F—Ph | 10 | 96 |

(τ represents the time to full conversion)

What is claimed is:

1. A compound of formula (4)

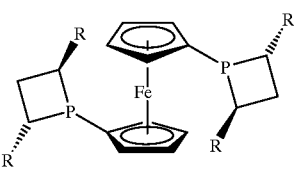

(4)

or the opposite enantiomer thereof, each enantiomerically enriched, wherein R is $C_{1-10}$ alkyl.

2. The compound, according to claim 1, wherein R is linear $C_{1-4}$ alkyl.

3. The compound, according to claim 2, wherein R is methyl or ethyl.

4. A transition metal complex of a compound of claim 1.

5. The complex, according to claim 4, wherein said transition metal is rhodium(I).

6. The complex, according to claim 5, which is of the formula [Rh(compound of formula 4)(COD)]BF$_4$.

7. A method for the stereoselective hydrogenation of a substrate, which is conducted in the presence of, as catalyst, a transition metal complex of a compound of claim 1.

8. The method, according to claim 7, wherein said substrate has the partial formula C═C(C═O)—C—C═O.

9. The method, according to claim 7, wherein said substrate has the partial formula C═C(COOH)—C—C═O.

* * * * *